United States Patent
Orten (10) Patent No.: US 6,624,551 B2
(45) Date of Patent: Sep. 23, 2003

(54) TWO-WAY MECHANO-ELECTRIC TRANSDUCER

(75) Inventor: Birger Orten, Ålesund (NO)

(73) Assignee: Meditron ASA, Vittre (NO)

( * ) Notice: Subject to any disclaimer, the term of this patent is extended or adjusted under 35 U.S.C. 154(b) by 6 days.

(21) Appl. No.: 09/788,607

(22) Filed: Aug. 2, 2001

(65) Prior Publication Data

US 2002/0030421 A1 Mar. 14, 2002

Related U.S. Application Data (60) Provisional application No. 60/213,477, filed on Jun. 23, 2000.

(51) Int. Cl.$^7$ ............................................. H01L 41/053
(52) U.S. Cl. ........................ 310/334; 310/322; 310/328; 310/329; 310/351
(58) Field of Search ........................ 310/322, 328–331, 310/338, 339, 348, 351

(56) References Cited

U.S. PATENT DOCUMENTS

| | | | | |
|---|---|---|---|---|
| 2,842,685 A | * | 7/1958 | Petermann et al. | 310/322 |
| 2,880,333 A | * | 3/1959 | Dranetz | 310/326 |
| 2,963,911 A | * | 12/1960 | Courtney-Pratt et al. | 310/329 |
| 3,069,573 A | * | 12/1962 | Van Liew | 310/351 |
| 3,147,391 A | * | 9/1964 | Darrel et al. | 310/329 |
| 4,349,183 A | * | 9/1982 | Wirt et al. | 267/160 |
| 4,398,116 A | * | 8/1983 | Lewis | 310/334 |
| 4,685,767 A | * | 8/1987 | Ueshiba et al. | 310/324 |
| 4,727,279 A | | 2/1988 | Peng | 310/329 |
| 4,779,985 A | * | 10/1988 | Wirt | 356/476 |
| 5,428,995 A | * | 7/1995 | Fersht et al. | 73/504.12 |
| 6,196,067 B1 | * | 3/2001 | Martin et al. | 73/514.32 |
| 6,222,306 B1 | * | 4/2001 | Groult et al. | 310/337 |
| 6,324,909 B1 | * | 12/2001 | Wyse et al. | 73/504.12 |
| 6,357,295 B1 | * | 3/2002 | Wyse | 73/504.04 |
| 6,359,370 B1 | * | 3/2002 | Chang | 310/328 |
| 6,411,010 B1 | * | 6/2002 | Suzuki et al. | 310/323.16 |

FOREIGN PATENT DOCUMENTS

| | | | | |
|---|---|---|---|---|
| DE | 4012829 A1 | * | 10/1991 | G01L/1/04 |
| EP | 0 118 329 A2 | | 9/1984 | H04R/17/00 |
| GB | 2166022 A | | 4/1986 | H04R/17/00 |
| JP | 7-143765 | | 6/1995 | H02N/2/00 |

* cited by examiner

Primary Examiner—Thomas M. Dougherty
(74) Attorney, Agent, or Firm—Wenderoth, Lind & Ponack, L.L.P.

(57) ABSTRACT

A transducer for emitting and picking up mechanical vibrations includes a center body (4) suspended in a piezo-electric and elastic suspension structure (3) in a surrounding framework (2). The suspension structure (3) is formed in sectors, and has separate signal wires for each respective sector (5) so that vibrations can be emitted and received at the same time with different sectors (5). In addition, the center body (4) can be equipped with piezo-elements of its own.

21 Claims, 7 Drawing Sheets fig. 1 fig. 3a fig. 3b fig. 4a fig. 4b fig. 5

TWO-WAY MECHANO-ELECTRIC TRANSDUCER

This application claims domestic priority under 35 U.S.C. §119 to Provisional Application Serial No. 60/213,477, filed Jun. 23, 2000.

BACKGROUND OF THE INVENTION

The present invention relates to emitting and sensing acoustical or mechanical vibration, concurrently while receiving and transmitting electrical signals corresponding to a vibration state parameter. In particular, the invention relates to a mechano-electrical transducer for emitting and sensing vibration, and for concurrent reception and transmission of at least one electrical signal that corresponds to the emitted or sensed vibration.

Transducers between electrical and mechanical energy (vibrations, force, acceleration) have many uses, and exist in various implementations. Often, two or three separate transducers are used, for example, sense acceleration in three orthogonal directions, by suspending massive bodies in springing systems so that they move relative to respective reference frameworks.

GB 2,055,018 and EP 118,329 teach known transducers with a massive body suspended centrally in piezoelectric flexible "lamellas", or in piezoelectric filaments, for seismic and acoustical detection applications.

Related art can also be found in GB 2,166,022, which teaches a transducer in the form of a loudspeaker (i.e., providing transformation from electrical to acoustical signals) and a massive body suspended centrally in a piezoelectric thin loudspeaker diaphragm that may be divided into several lamella-like areas by radial slits. Since it is common knowledge that a loudspeaker can also be utilized as a microphone, the GB 2,055,018 publication must be regarded as showing a bidirectional transducer. The point of the central body in the publication is that it will be possible to lower the useful frequency range of the loudspeaker by adding such a center mass.

SUMMARY OF THE INVENTION

The present invention aims at providing a bidirectional transducer that, better than previously known solutions, is able to operate with a directional effect and provide improved emission and detection, particularly in connection with echo measurements in biological tissue.

Hence, in accordance with the invention there is provided a mechanoelectric two-way transducer as described below. Preferable embodiments of the invention are also described below.

BRIEF DESCRIPTION OF THE DRAWINGS

In the following, the invention shall be illuminated in more detail by examining some exemplary embodiments with reference to the appended drawings, in which.

DETAILED DESCRIPTION OF THE INVENTION

Figure 1:
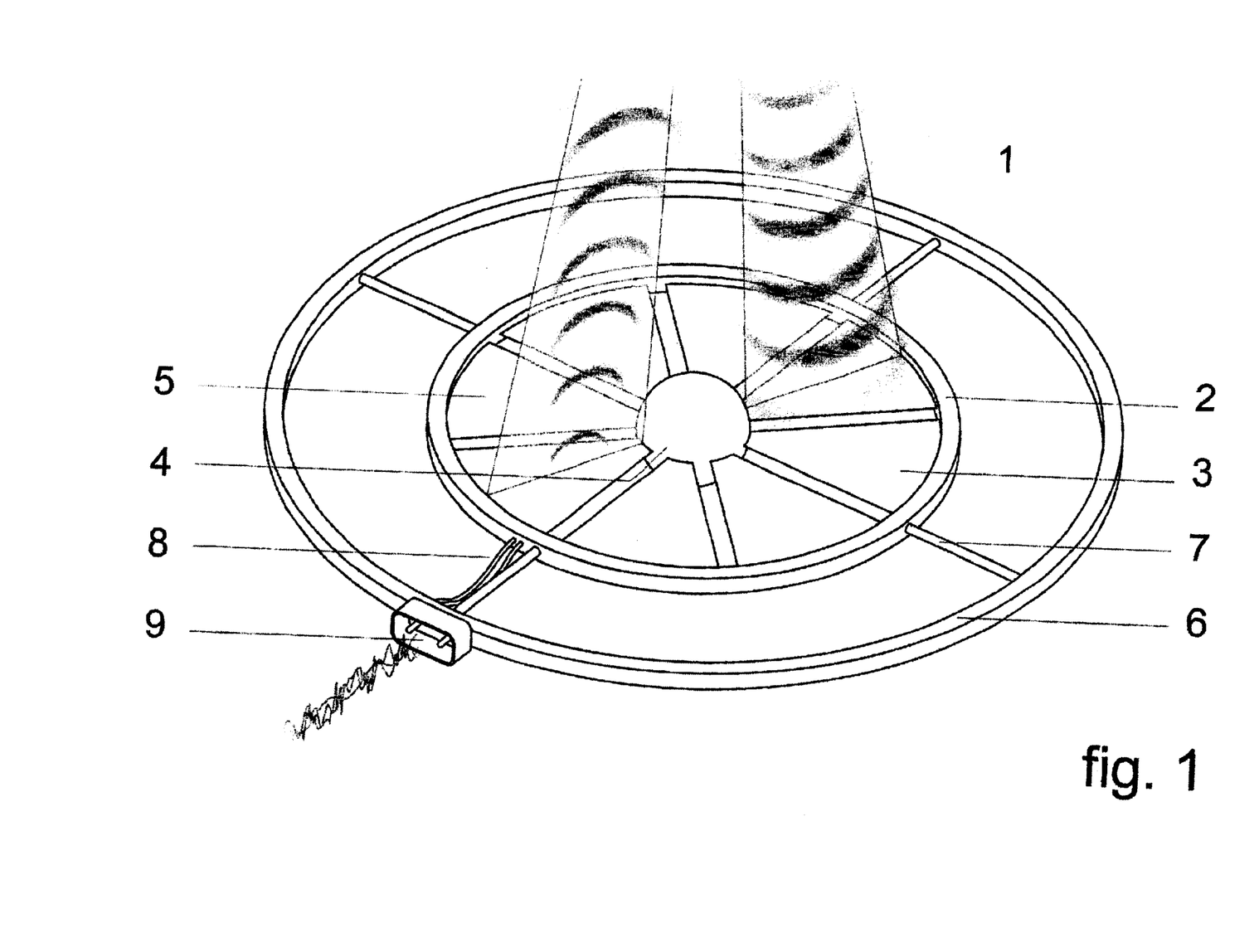
FIG. 1 shows a first embodiment of the transducer in accordance with the invention, with transmit and receive activity in suspension sectors.

FIG. 1 shows a first embodiment of the transducer 1 in accordance with the invention. A center body 4 is suspended in an annular framework (inner ring) 2 in a planar suspension structure 3 comprising a number of elastic and sector-shaped sheets 5, in this case eight such sectors 5.

In the embodiment shown in FIG. 1, the framework 2 is, in turn, suspended in an outer frame 6 by an outer, elastic suspension structure in the form of elastic strings 7. However, the outer frame 6 with the outer suspension structure is not obligatory for the invention.

Signal wires 8 lead to and from the sectors 5, and possibly to and from the center body 4, and a connector 9 is provided on the outer frame 6. The wires 8 are not shown in detail further inside the framework 2, but lead to and from each respective sector 5, and possibly to and from the center body 4.

Every sector sheet 5 can be attached at the outer edge between two sections of ring 2, and can be attached at the inner "tip" between two hemispheres that constitute the center body 4. The sector sheets 5 are, for example, made from PVDF (Polyvinylidene fluoride), which is a material having piezoelectric properties, and which material is able to convert an electrical input signal to a vibration that may propagate to a medium in front of (above) the transducer, for example body tissue. The material is also able to convert incoming vibration waves hitting a sector (or several sectors), to electrical output signals. Every sector 5 is separately addressable with separate wires 8.

In this first embodiment, the center body 4 is simply a solid body that, when the transducer is mounted as a front part of, for example a handheld examination unit, will engage, for example, the skin surface of a patient such that the central part of the transducer will be pushed rearwardly. This causes the sectors 5 to be somewhat angled in relation to the unloaded position. Consequently, a focusing effect is achieved, such as indicated in FIG. 1. It should also be noted that with an elastic outer suspension structure 7, such as indicated in FIG. 1, some rearward deflection will occur there also. In an embodiment without such an outer structure, the deflection angle of the sectors will be greater.

Using a transducer of the type shown here, it will be possible to transmit vibrations with one or some sectors at the same time as another sector, or some other sectors, receive reflected vibrations (i.e. an echo).

Another advantage is the ability to remove undesired signals, i.e. noise, using signals received from different sectors in post-processing. In addition, it is also possible to connect a noise signal in opposite phase to the signal wires leading to one particular sector in order to cancel the noise part of the signal received by that sector. The noise signal that is coupled in may, for instance, originate from a piezo-element arranged on the outer suspension structure 7, which structure receives an incoming noise signal, or may originate from a separately arranged sensor.

Figure 2:
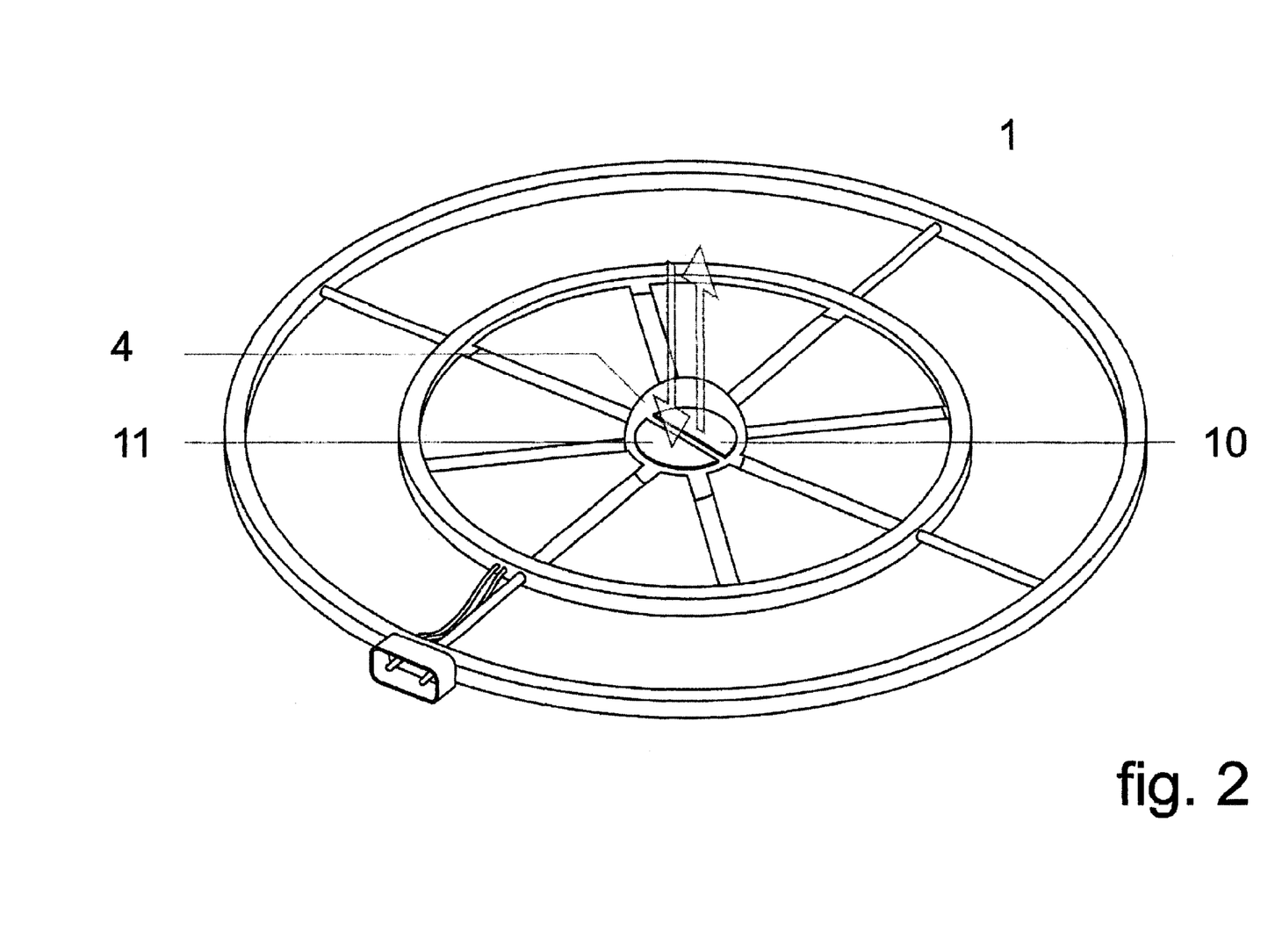
FIG. 2 shows an embodiment with an active center body.

In the embodiment appearing in FIG. 2, the center body 4 is "active" also. In other words, the centre body itself contains piezo-elements 10 and 11, such as a piezo-element 10 for transmitting vibrations, and a piezo-element 11 for receiving reflected vibrations. The remaining portions of the transducer are as described in connection with FIG. 1. The signal wires to the piezo-elements of the center body are not shown in FIG. 2, but they follow paths on the sectors 5 up to the center body 4.

In the shown embodiment, the piezo-elements 10 and 11 are cast-in "half-moons" of piezo-material. The manner of using such an embodiment as discussed here will, for example, be that the piezo-element 10 of the center body transmits high frequency vibrations, generally in the range 5–10 MHz (however not limited to this range), in order to make an echo Doppler investigation. Reflected vibrations are picked up by element 11. Simultaneously with the echo Doppler investigation of center body 4, the sectors 5, or some of them, can be used for ordinary auscultation (i.e. purely for listening to acoustical vibrations from a body).

Figure 3A:
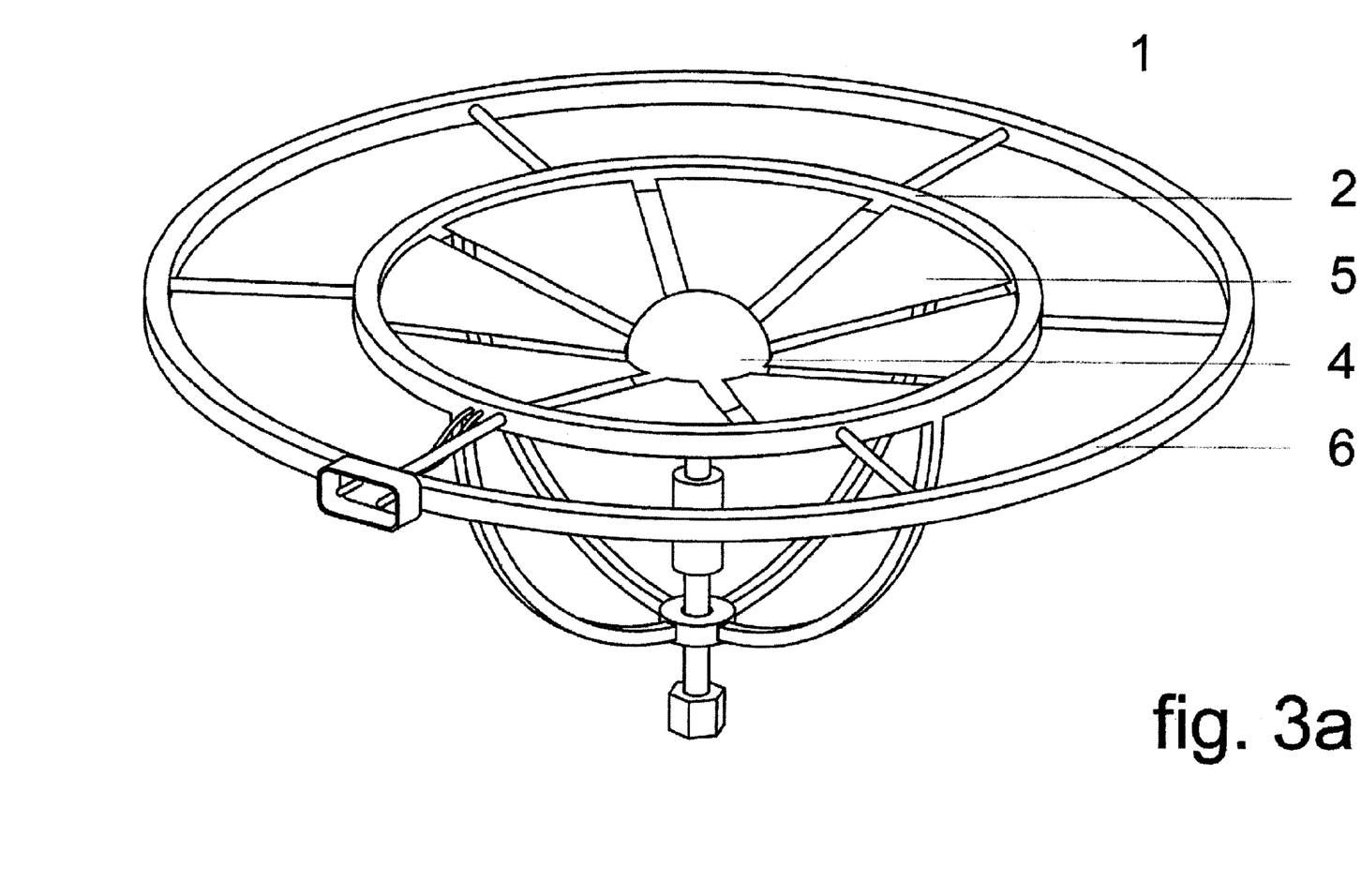
FIGS. 3a and 3b show a first embodiment with a tautening structure for the center body.
Figure 3B:
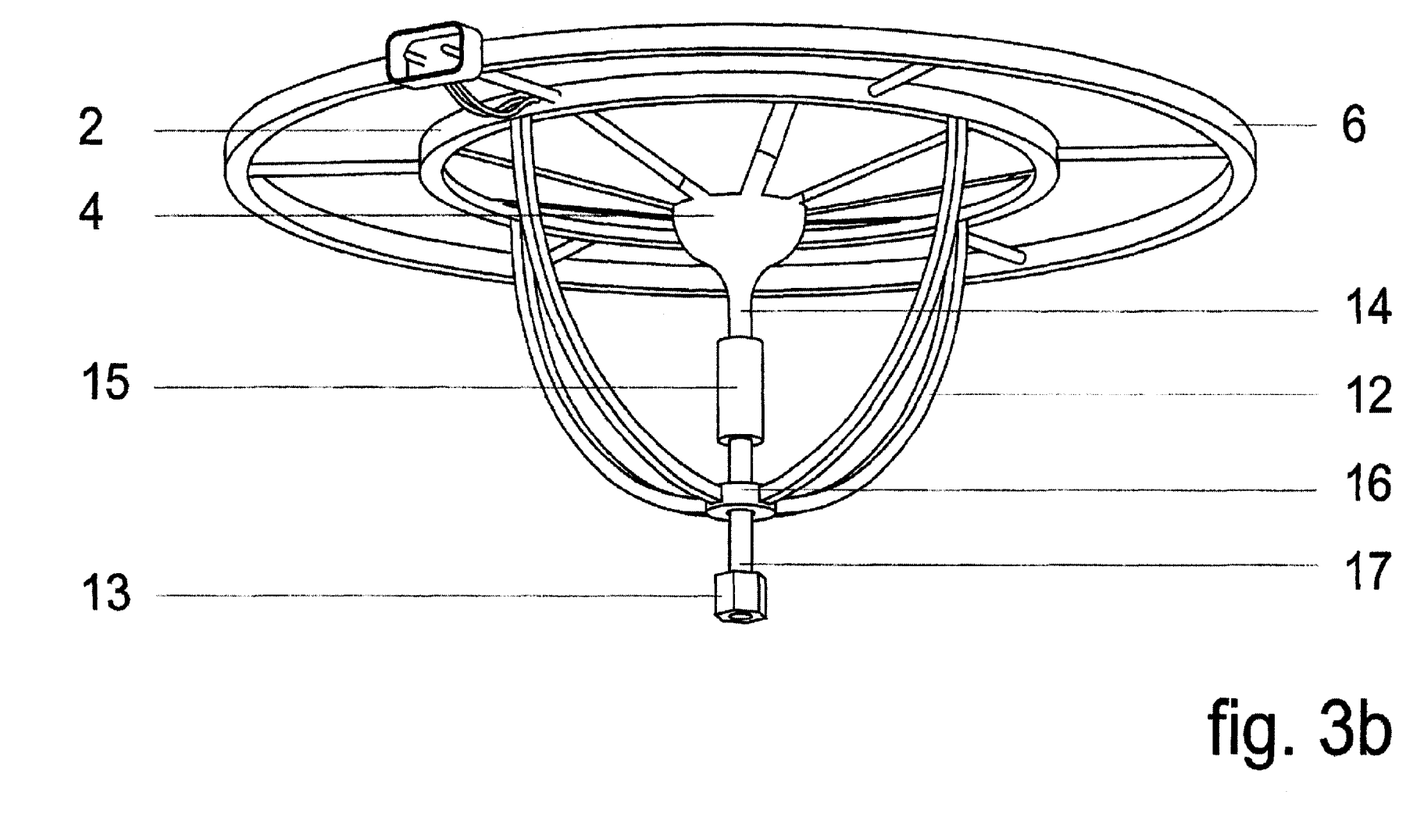

FIGS. 3a and 3b show an embodiment of the transducer in accordance with the invention, in which it is possible to change and keep a check on the slant angle of the sectors (referring to the slant angle mentioned above, obtained by pushing the center body 4 against a surface). This is achieved by designing the center body 4 with an extended rear member 14 that is held by a sleeve 15 in such a manner that this sleeve 15 can rotate around a lower (not shown) ball or enlargement on the rear member 14. Therefore, the rear member (and consequently the center body) can be pulled down when the sleeve 15 travels down while rotating. The rotating travel in a downward direction is caused by rotating head 13 and a threaded member 16 (threaded inside), held by a number of stays 12, that cooperate with threads on bolt 17 to provide a vertical travel. In this manner, it is possible to regulate the slant angle and the tensioning of the sectors 5.

Figure 4A:
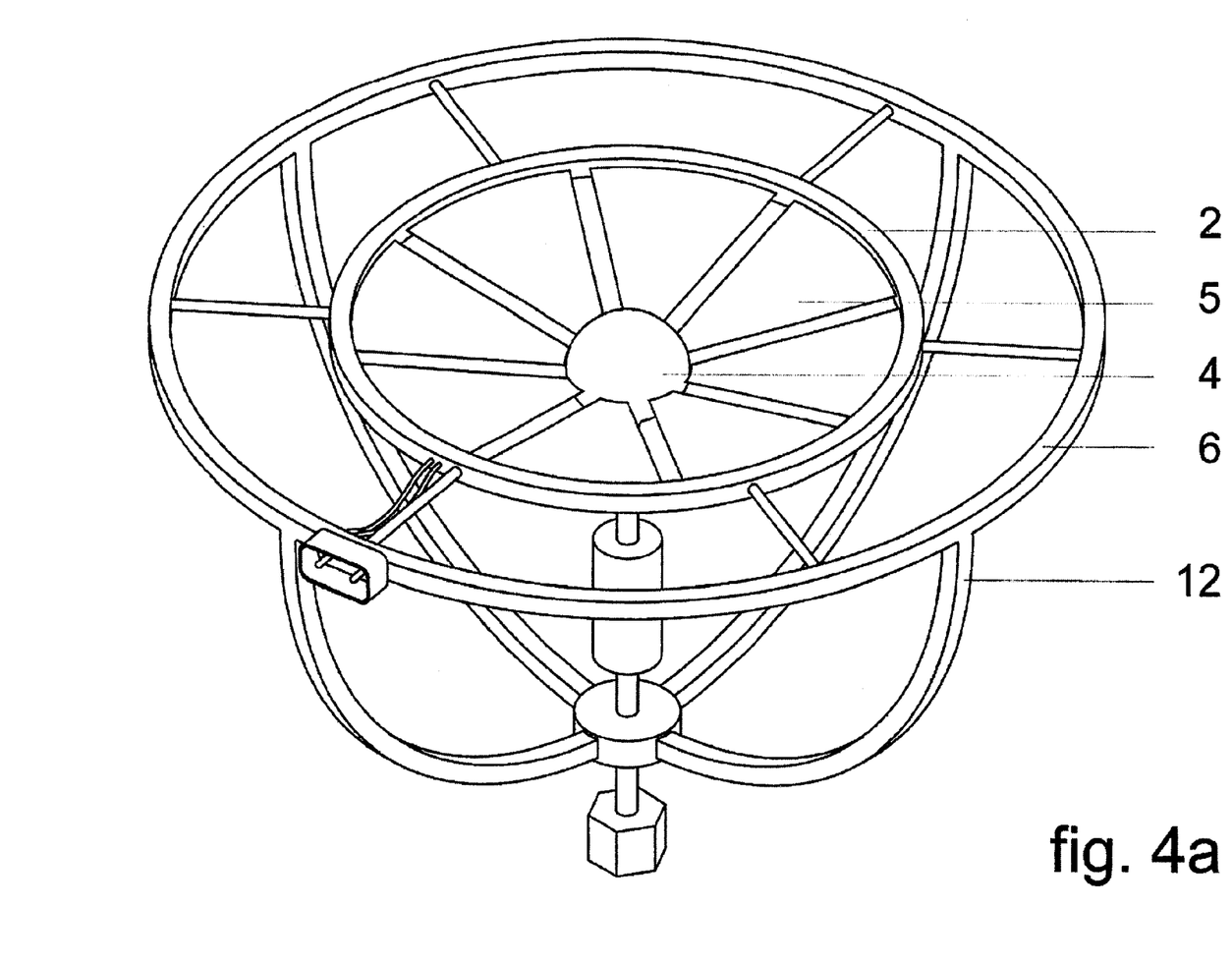
FIGS. 4a and 4b show a second embodiment with a tautening structure for the center body.
Figure 4B:
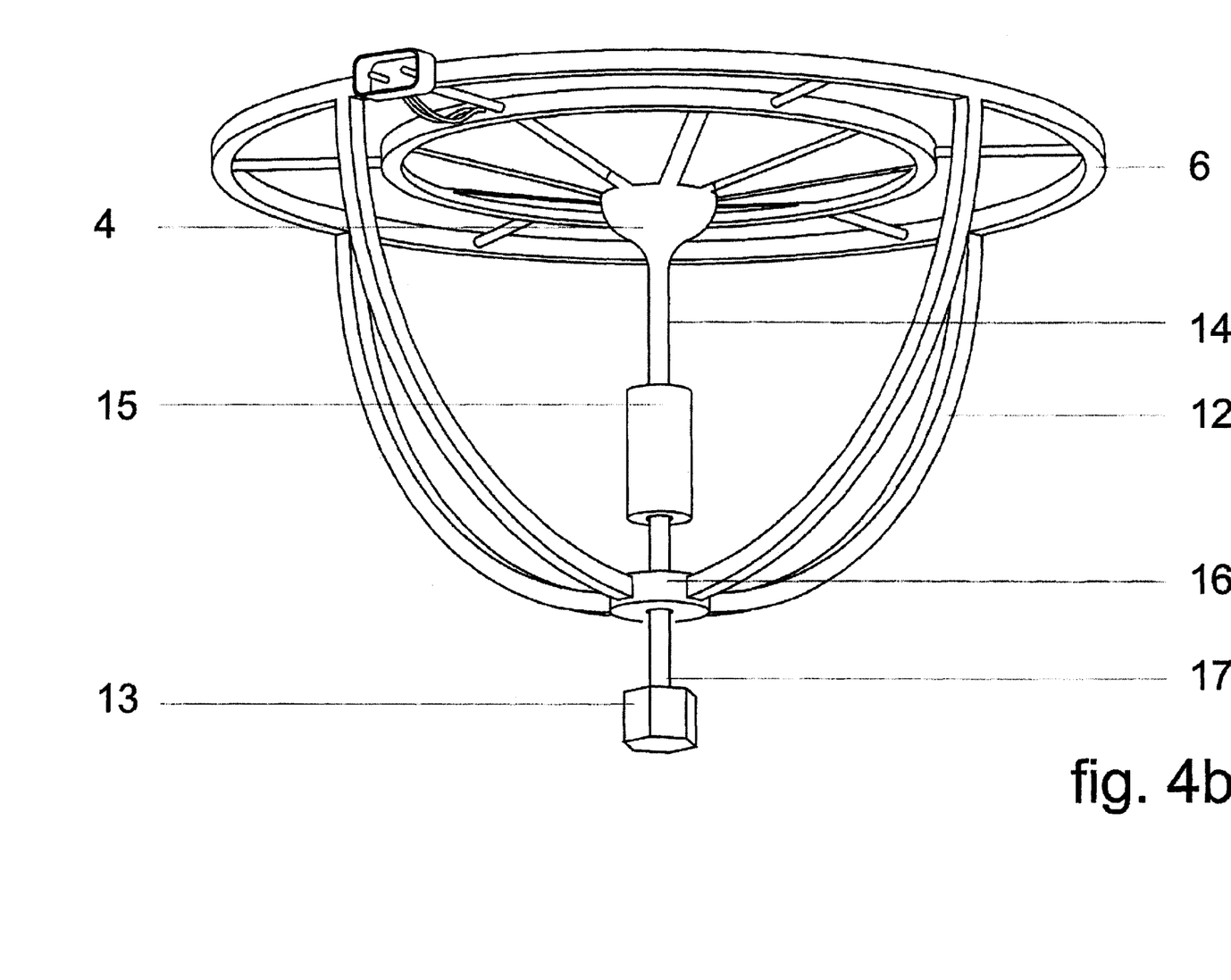

As indicated in FIGS. 3a, b, the stays 12 are attached to the inner ring 2, so that the tensioning will influence only the main part of the transducer with sectors 5. FIGS. 4a and 4b, however, show a variant in which the stays 12 are attached to the outer ring 6. This means that the outer suspension structure (i.e., inner ring) will be tensioned and set in a slanting angle by means of the adjustment system 12–17.

The curved shape of the stays 12 is practical, but not mandatory.

The transducer embodiments shown in FIGS. 3 and 4 are intended to operate along the same principles as mentioned regarding the embodiments of FIGS. 1 and 2.

Figure 5:
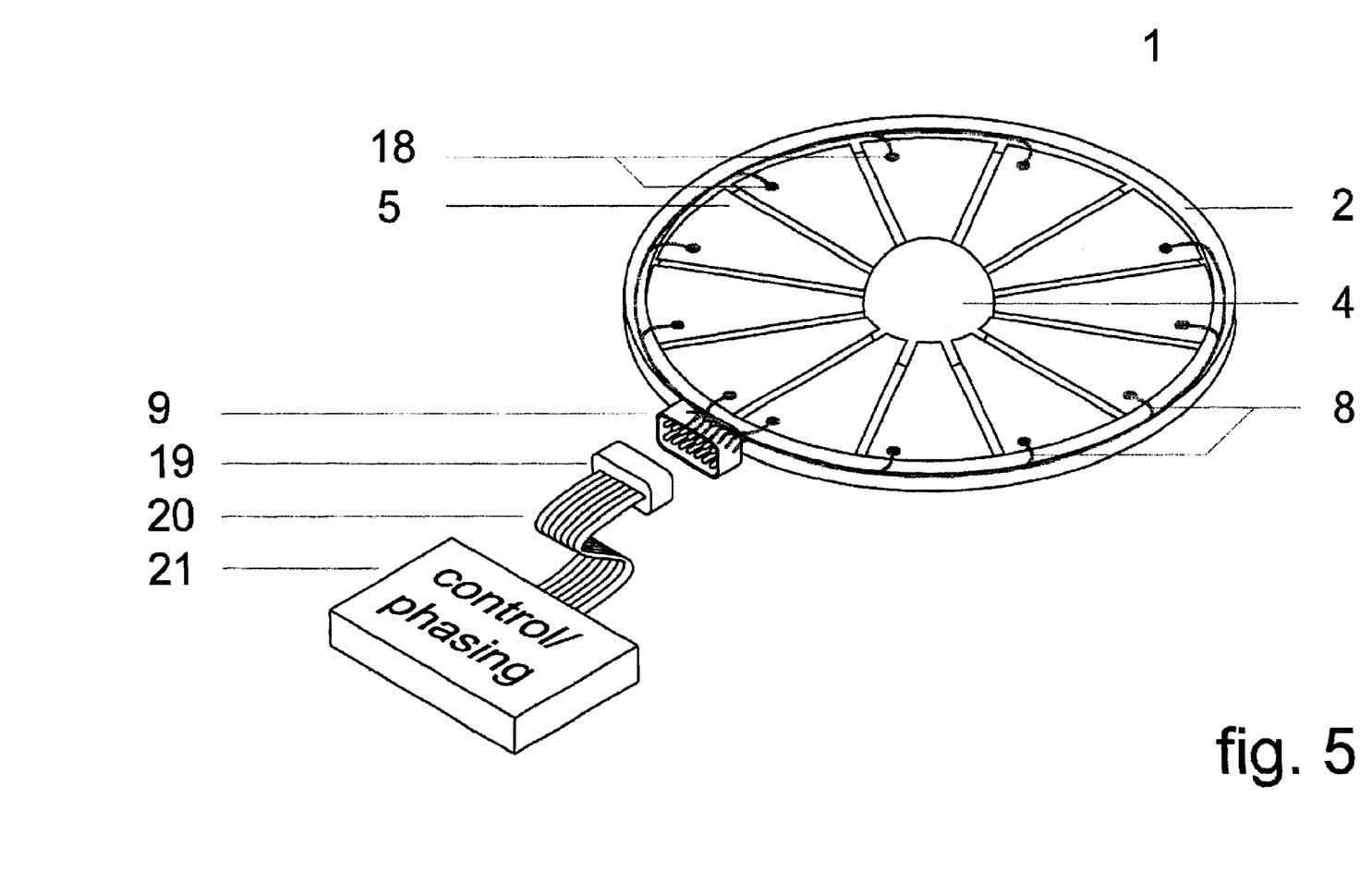
FIG. 5 shows, schematically, an embodiment with signal phasing.

FIG. 5 shows, schematically, an embodiment in which it is possible to provide, by controlling the signals applied to the respective piezoelectric sectors 5 in a detailed manner, further enhanced directional control of an emitted mechanical oscillatory wave. One will then use a principle that is known from antenna technology, for example within the art of cellular telephony, wherein antennas consisting of a plurality of antenna elements are "fired" with small mutual delays or phase shifts so that constructive interference is achieved in a desired direction outward from the total antenna. This principle is also used when receiving/listening (i.e. "listening windows") are opened in attached receiver electronics in "phased succession", and part signals are added so as to effectively listen in certain directions.

Consequently, directional and phased emission of mechanical vibration waves are provided by making a control unit 21 supply phase-shifted (and possibly intensity-adjusted) signals to the sectors 5 via the multiwire cable 20 and the multi-connectors 19 and 9 and wires 8, to contact points 18 on every sector, to provide phase-controlled signals for the sectors. Further detailed control can possibly be achieved by additional radial sectioning of the active piezoelectric sector areas, and with a separate signal supply thereto. The signal wires 8 and contact points 18 are only shown in a schematical manner. For example, all wires 8 have not been shown to be leading all the way to the connector 9, but of course this is the intention. In FIG. 5, the transducer is, for simplicity, shown without an outer frame, but such an outer frame 6 as in the other figures can of course also be used in the "phased" embodiment.

Reception/listening can of course also be done in accordance with the same phasing principle. A computer unit in the control unit 21 handles the signal phasing in emission as well as in reception, in accordance with programmed algorithms.

What is claimed is:

1. A two-way mechano-electric transducer, comprising:
   a frame;
   a piezoelectric suspension structure suspended in said frame, said suspension structure including a plurality of elastic sectors;
   a center body suspended in said piezoelectric suspension structure; and
   a plurality of signal wires arranged such that at least one of said signal wires is connected to each of said elastic sectors of said suspension structure, said suspension structure and said center body being operable to substantially simultaneously transmit mechanical vibrations and receive mechanical vibrations.

2. The transducer of claim 1, wherein at least a first one of said elastic sectors of said suspension structure is operable to transmit mechanical vibrations while at least a second one of said elastic sectors of said suspension structure receives in echo vibration signal based on the mechanical vibrations transmitted by said at least a first one of said elastic sectors.

3. The transducer of claim 2, wherein said center body and said suspension structure are arranged so that when said center body is moved by being pushed against a surface, said elastic sectors of said suspension structure are tensioned so as to be slanted with respect to a plane of said frame, thereby enhancing a directivity of signal emission and signal reception.

4. The transducer of claim 1, wherein said center body includes a piezo-element for transmitting mechanical vibrations.

5. The transducer of claim 4, wherein said piezo-element comprises a first piezo-element, said center body further including a second piezo-element for receiving mechanical vibrations.

6. The transducer of claim 5, wherein said first piezo-element is operable to transmit ultrasound signals having a frequency range of 5 MHz to 10 MHz, and said second piezo-element is operable to receive reflections of the ultrasound signals transmitted by said first piezo-element so as to perform an echo Doppler investigation.

7. The transducer of claim 6, wherein said first piezo-element is operable to transmit the ultrasound signals and the second piezo-element is operable to receive the reflections of the ultrasound signals, simultaneously with auscultation by at least one of said elastic sectors of said suspension structure.

8. The transducer of claim 5, wherein a group of said elastic sectors are operable to receive mechanical vibration signals, said group of elastic sectors being interconnected for electronic combination of signals and cancellation of undesired frequencies.

9. The transducer of claim 8, wherein said second piezo-element is connected with said group of elastic sectors for electronic combination of signals and cancellation of undesired frequencies.

10. The transducer of claim 5, wherein said frame comprises an inner frame, a group of said elastic sectors being operable to receive mechanical vibration signals, said transducer further comprising an outer frame including an outer elastic suspension structure suspending said inner frame, said outer suspension structure having a third piezo-element for generating receive signals, said third piezo-element being connected with said group of elastic sectors for electronic combination of signals and cancellation of undesired frequencies.

11. The transducer of claim 10, wherein said third piezo-element is further connected with said second piezo-element for electronic combination of signals and cancellation of undesired frequencies.

12. The transducer of claim 5, wherein a group of said elastic sectors is operable to receive mechanical vibration signals, said transducer further comprising an external sensor for generating receive signals, said external sensor being connected with said group of elastic sectors for electronic combination of signals and cancellation of undesired frequencies.

13. The transducer of claim 1, wherein a group of said elastic sectors are operable to receive mechanical vibration signals, said group of elastic sectors being interconnected for electronic combination of signals and cancellation of undesired frequencies.

14. The transducer of claim 13, wherein said center body includes a piezo-element for receiving mechanical vibrations, said piezo-element being connected with said group of elastic sectors for electronic combination of signals and cancellation of undesired frequencies.

15. The transducer of claim 1, wherein said frame comprises an inner frame, a group of said elastic sectors being operable to receive mechanical vibration signals, said transducer further comprising an outer frame including an outer elastic suspension structure suspending said inner frame, said outer suspension structure having a piezo-element for generating receive signals, said piezo-element being connected with said group of elastic sectors for electronic combination of signals and cancellation of undesired frequencies.

16. The transducer of claim 15, wherein said piezo-element comprises a first piezo-element, said center body including a second piezo-element for receiving mechanical vibrations, said first piezo-element being further connected with said second piezo-element for electronic combination of signals and cancellation of undesired frequencies.

17. The transducer of claim 1, wherein a group of said elastic sectors is operable to receive mechanical vibration signals, said transducer further comprising an external sensor for generating receive signals, said external sensor being connected with said group of elastic sectors for electronic combination of signals and cancellation of undesired frequencies.

18. The transducer of claim 1, further comprising a controller electrically connected to said elastic sectors for phasing signals to and from said elastic sectors so as to achieve directional emission and reception.

19. The transducer of claim 1, further comprising a tensioning structure connected to said center body at a rear side of said suspension structure, said tensioning structure being operable to pull said center body toward the rear side so as to tension and angle said elastic sectors.

20. The transducer of claim 19, wherein said tensioning structure is fixed to said frame.

21. The transducer of claim 19, wherein said frame comprises an inner frame, said transducer further comprising an outer frame including an outer elastic suspension structure suspending said inner frame, said tensioning structure being fixed to said outer frame such that said tensioning structure is operable to pull said center body toward the rear side so as to tension and angle said elastic sectors and said outer elastic suspension structure.

* * * * *